(12) United States Patent
Chen et al.

(10) Patent No.: US 7,072,701 B2
(45) Date of Patent: Jul. 4, 2006

(54) METHOD FOR SPECTROPHOTOMETRIC BLOOD OXYGENATION MONITORING

(75) Inventors: Bo Chen, Derby, CT (US); Paul B. Benni, Stamford, CT (US)

(73) Assignee: CAS Medical Systems, Inc., Branford, CT (US)

( * ) Notice: Subject to any disclaimer, the term of this patent is extended or adjusted under 35 U.S.C. 154(b) by 185 days.

(21) Appl. No.: 10/628,068

(22) Filed: Jul. 24, 2003

(65) Prior Publication Data

US 2004/0024297 A1    Feb. 5, 2004

Related U.S. Application Data

(60) Provisional application No. 60/407,277, filed on Aug. 30, 2002, provisional application No. 60/398,937, filed on Jul. 26, 2002.

(51) Int. Cl.
*A61B 5/00* (2006.01)
(52) U.S. Cl. .................................... 600/331
(58) Field of Classification Search ................ 600/323, 600/331, 336; 250/339.09, 341.1, 341.5; 356/41, 319
See application file for complete search history.

(56) References Cited

U.S. PATENT DOCUMENTS

| | | |
|---|---|---|
| 3,638,640 A | 2/1972 | Shaw |
| 3,674,008 A | 7/1972 | Johnson |
| 4,105,021 A | 8/1978 | Williams et al. |
| 4,206,764 A | 6/1980 | Williams |
| 4,223,680 A | 9/1980 | Jobsis |
| 4,281,645 A | 8/1981 | Jobsis |
| 4,321,930 A | 3/1982 | Jobsis et al. |
| 4,380,240 A | 4/1983 | Jobsis et al. |
| 4,510,938 A | 4/1985 | Jobsis et al. |
| 4,570,638 A | 2/1986 | Stoddart et al. |
| 4,621,643 A | 11/1986 | New, Jr. et al. |
| 4,690,492 A | 9/1987 | Beard |
| 4,700,708 A | 10/1987 | New, Jr. et al. |
| 4,725,147 A | 2/1988 | Stoddart |
| 4,768,516 A | 9/1988 | Stoddart et al. |
| 4,770,179 A | 9/1988 | New, Jr. et al. |
| 4,805,623 A | 2/1989 | Jöbsis |

(Continued)

*Primary Examiner*—Eric F. Winakur
(74) *Attorney, Agent, or Firm*—O'Shea, Getz & Kosakowski, P.C.

(57) ABSTRACT

A method and apparatus for non-invasively determining the blood oxygen saturation level within a subject's tissue is provided that utilizes a near infrared spectrophotometric (NIRS) sensor capable of transmitting a light signal into the tissue of a subject and sensing the light signal once it has passed through the tissue via transmittance or reflectance. The method includes the steps of: (1) transmitting a light signal into the subject's tissue, wherein the transmitted light signal includes a first wavelength, a second wavelength, and a third wavelength; (2) sensing a first intensity and a second intensity of the light signal, along the first, second, and third wavelengths after the light signal travels through the subject at a first and second predetermined distance; (3) determining an attenuation of the light signal for each of the first, second, and third wavelengths using the sensed first intensity and sensed second intensity of the first, second, and third wavelengths; (4) determining a difference in attenuation of the light signal between the first wavelength and the second wavelength, and between the first wavelength and the third wavelength; and (5) determining the blood oxygen saturation level within the subject's tissue using the difference in attenuation between the first wavelength and the second wavelength, and the difference in attenuation between the first wavelength and the third wavelength.

50 Claims, 3 Drawing Sheets

U.S. PATENT DOCUMENTS

| | | |
|---|---|---|
| 4,817,623 A | 4/1989 | Stoddart et al. |
| 4,848,901 A | 7/1989 | Hood, Jr. |
| 4,865,038 A | 9/1989 | Rich et al. |
| 4,907,876 A | 3/1990 | Suzuki et al. |
| 4,913,150 A | 4/1990 | Cheung et al. |
| 4,942,877 A | 7/1990 | Sakai et al. |
| 5,054,488 A | 10/1991 | Muz |
| 5,057,695 A * | 10/1991 | Hirao et al. ................ 600/310 |
| 5,058,588 A | 10/1991 | Kaestle |
| 5,080,098 A | 1/1992 | Willett et al. |
| 5,088,493 A | 2/1992 | Giannini et al. |
| 5,139,025 A | 8/1992 | Lewis et al. |
| 5,140,989 A | 8/1992 | Lewis et al. |
| 5,153,669 A | 10/1992 | DeGroot |
| 5,217,013 A | 6/1993 | Lewis et al. |
| 5,218,962 A | 6/1993 | Mannheimer et al. |
| 5,277,181 A | 1/1994 | Mendelson et al. |
| 5,349,961 A | 9/1994 | Stoddart et al. |
| 5,353,791 A | 10/1994 | Tamura et al. |
| 5,421,329 A | 6/1995 | Casciani et al. |
| 5,465,714 A | 11/1995 | Scheuing |
| 5,477,853 A | 12/1995 | Farkas et al. |
| 5,482,034 A | 1/1996 | Lewis et al. |
| 5,517,987 A | 5/1996 | Tsuchiya |
| 5,520,177 A | 5/1996 | Ogawa et al. |
| 5,524,617 A | 6/1996 | Mannheimer |
| 5,529,065 A | 6/1996 | Tsuchiya |
| 5,542,421 A | 8/1996 | Erdman |
| 5,584,296 A | 12/1996 | Cui et al. |
| 5,632,273 A | 5/1997 | Suzuki |
| 5,661,302 A | 8/1997 | Evans et al. |
| 5,676,142 A | 10/1997 | Miwa et al. |
| 5,694,931 A | 12/1997 | Tsuchiya |
| 5,697,367 A | 12/1997 | Lewis et al. |
| 5,720,284 A | 2/1998 | Aoyagi et al. |
| 5,729,333 A | 3/1998 | Osten et al. .................. 356/39 |
| 5,746,206 A | 5/1998 | Mannheimer |
| 5,752,914 A | 5/1998 | Delonzor et al. |
| 5,758,644 A | 6/1998 | Diab et al. |
| 5,770,454 A | 6/1998 | Essenpreis et al. |
| 5,782,755 A | 7/1998 | Chance et al. |
| 5,795,292 A | 8/1998 | Lewis et al. |
| 5,803,909 A | 9/1998 | Maki et al. |
| 5,853,370 A | 12/1998 | Chance et al. |
| 5,879,294 A | 3/1999 | Anderson et al. |
| 5,902,235 A | 5/1999 | Lewis et al. |
| 5,987,351 A | 11/1999 | Chance |
| 6,192,260 B1 | 2/2001 | Chance ....................... 600/310 |
| 6,615,065 B1 | 9/2003 | Barrett et al. |
| 2005/0119542 A1 | 6/2005 | Stoddart et al. |

* cited by examiner

METHOD FOR SPECTROPHOTOMETRIC BLOOD OXYGENATION MONITORING

This application claims the benefit of the filing date of U.S. Provisional Applications 60/398,937, filed Jul. 26, 2002, and 60/407,277 filed Aug. 30, 2002.

This invention was made with Government support under Contract No. 1R43NS045488-01 awarded by the Department of Health & Human Services. The Government has certain rights in the invention.

BACKGROUND OF THE INVENTION

1. Technical Field

This invention relates to methods for non-invasively determining biological tissue oxygenation in general, and to non-invasive methods utilizing near-infrared spectroscopy (NIRS) techniques in particular.

2. Background Information.

The molecule that carries the oxygen in the blood is hemoglobin. Oxygenated hemoglobin is called oxyhemoglobin ($HbO_2$) and deoxygenated hemoglobin is deoxyhemoglobin (Hb). Total hemoglobin is the summation of the two states of hemoglobin (Total Hb=$HbO_2$+Hb), and is proportional to relative blood volume changes, provided that the hematocrit or hemoglobin concentration of the blood is unchanged. The mammalian cardiovascular system consists of a blood pumping mechanism (the heart), a blood transportation system (blood vessels), and a blood oxygenation system (the lungs). Blood oxygenated by the lungs passes through the heart and is pumped into the arterial vascular system. Under normal conditions, oxygenated arterial blood consists predominately of $HbO_2$. Large arterial blood vessels branch off into smaller branches called arterioles, which profuse throughout biological tissue. The arterioles branch off into capillaries, the smallest blood vessels. In the capillaries, oxygen carried by hemoglobin is transported to the cells in the tissue, resulting in the release of oxygen molecules ($HbO_2 \rightarrow Hb$). Under normal conditions, only a fraction of the $HbO_2$ molecules give up oxygen to the tissue, depending on the cellular metabolic need. The capillaries then combine together into venuoles, the beginning of the venous circulatory system. Venuoles then combine into larger blood vessels called veins. The veins further combine and return to the heart, and then venous blood is pumped to the lungs. In the lungs, deoxygenated hemoglobin Hb collects oxygen becoming $HbO_2$ again and the circulatory process is repeated.

Oxygen saturation is defined as:

$$O_2 \text{ saturation } \% = \frac{HbO_2}{(HbO_2 + Hb)} * 100\% \quad \text{(Eqn. 1)}$$

In the arterial circulatory system under normal conditions, there is a high proportion of $HbO_2$ to Hb, resulting in an arterial oxygen saturation (defined as $SaO_2$ %) of 95–100%. After delivery of oxygen to tissue via the capillaries, the proportion of $HbO_2$ to Hb decreases. Therefore, the measured oxygen saturation of venous blood (defined as $SvO_2$ %) is lower and may be about 70%.

One spectrophotometric method, called pulse oximetry, determines arterial oxygen saturation ($SaO_2$) of peripheral tissue (i.e. finger, ear, nose) by monitoring pulsatile optical attenuation changes of detected light induced by pulsatile arterial blood volume changes in the arteriolar vascular system. The method of pulse oximetry requires pulsatile blood volume changes in order to make a measurement. Since venous blood is not pulsatile, pulse oximetry cannot provide any information about venous blood.

Near-infrared spectroscopy (NIRS) is an optical spectrophotometric method of continually monitoring tissue oxygenation that does not require pulsatile blood volume to calculate parameters of clinical value. The NIRS method is based on the principle that light in the near-infrared range (700 to 1,000 nm) can pass easily through skin, bone and other tissues where it encounters hemoglobin located mainly within micro-circulation passages; e.g., capillaries, arterioles, and venuoles. Hemoglobin exposed to light in the near infra-red range has specific absorption spectra that varies depending on its oxidation state; i.e., oxyhemoglobin ($HbO_2$) and deoxyhemoglobin (Hb) each act as a distinct chromophore. By using light sources that transmit near-infrared light at specific different wavelengths, and measuring changes in transmitted or reflected light attenuation, concentration changes of the oxyhemoglobin ($HbO_2$) and deoxyhemoglobin (Hb) can be monitored. The ability to continually monitor cerebral oxygenation levels is particularly valuable for those patients subject to a condition in which oxygenation levels in the brain may be compromised, leading to brain damage or death.

The apparatus used in NIRS analysis typically includes a plurality of light sources, one or more light detectors for detecting reflected or transmitted light, and a processor for processing signals that represent the light emanating from the light source and the light detected by the light detector. Light sources such as light emitting diodes (LEDs) or laser diodes that produce light emissions in the wavelength range of 700–1000 nm at an intensity below that which would damage the biological tissue being examined are typically used. A photodiode or other light source detector is used to detect light reflected from or passed through the tissue being examined. The processor takes the signals from the light sources and the light detector and analyzes those signals in terms of their intensity and wave properties.

It is known that relative changes of the concentrations of $HbO_2$ and Hb can be evaluated using apparatus similar to that described above, including a processor programmed to utilize a variant of the Beer-Lambert Law, which accounts for optical attenuation in a highly scattering medium like biological tissue. The modified Beer-Lambert Law can be expressed as:

$$A_\lambda = -\log(I/I_o)_\lambda = \alpha_\lambda * C * d * B_\lambda + G \quad \text{(Eqn.2)}$$

wherein "$A_\lambda$" represents the optical attenuation in tissue at a particular wavelength λ (units: optical density or OD); "$I_o$" represents the incident light intensity (units: W/cm$^2$); "I" represents the detected light intensity; "$\alpha_\lambda$" represents the wavelength dependent absorption coefficient of the chromophore (units: $OD*cm^{-1}*\mu M^{-1}$); "C" represents the concentration of chromophore (units: μM); "d" represents the light source to detector (optode) separation distance (units: cm); "$B_\lambda$" represents the wavelength dependent light scattering differential pathlength factor (unitless); and "G" represents light attenuation due to scattering within tissue (units: OD). The product of "$d*B_\lambda$" represents the effective pathlength of photon traveling through the tissue.

Absolute measurement of chromophore concentration (C) is very difficult because G is unknown or difficult to ascertain. However, over a reasonable measuring period of several hours to days, G can be considered to remain constant, thereby allowing for the measurement of relative changes of chromophore from a zero reference baseline. Thus, if time $t_1$ marks the start of an optical measurement (i.e., a base line) and time $t_2$ is an arbitrary point in time after $t_1$, a change in attenuation ($\Delta A$) between $t_1$ and $t_2$ can be calculated, and variables G and $I_o$ will cancel out providing that they remain constant.

The change in chromophore concentration ($\Delta C = C(t_2) - C(t_1)$) can be determined from the change in attenuation $\Delta A$, for example using the following equation derived from the modified Beer-Lambert Law:

$$\Delta A_\lambda = -\log (I_{t2}/I_{t1})_\lambda = \alpha_\lambda * \Delta C * d * B_\lambda \qquad (\text{Eqn.3})$$

Presently known NIRS algorithms that are designed to calculate the relative change in concentration of more than one chromophore use a multivariate form of Equation 2 or 3. To distinguish between, and to compute relative concentration changes in, oxyhemoglobin ($\Delta HbO_2$) and deoxyhemoglobin ($\Delta Hb$), a minimum of two different wavelengths are typically used. The concentration of the $HbO_2$ and $Hb$ within the examined tissue is determined in µmoles per liter of tissue (µM).

The above-described NIRS approach to determining oxygenation levels is useful, but it is limited in that it only provides information regarding a change in the level of oxygenation within the tissue. It does not provide a means for determining the absolute value of oxygen saturation within the biological tissue.

At present, information regarding the relative contributions of venous and arterial blood within tissue examined by NIRS is either arbitrarily chosen or is determined by invasive sampling of the blood as a process independent from the NIRS examination. For example, It has been estimated that NIRS examined brain tissue comprising about 60 to 80% blood venous and about 20 to 40% arterial blood. Blood samples from catheters placed in venous drainage sites such as the internal jugular vein, jugular bulb, or sagittal sinus have been used to evaluate NIRS measurements. Results from animal studies have shown that NIRS interrogated tissue consists of a mixed vascular bed with a venous-to-arterial ratio of about 2:1 as determined from multiple linear regression analysis of sagittal sinus oxygen saturation ($SssO_2$) and arterial oxygen saturation ($SaO_2$). An expression representing the mixed venous/arterial oxygen saturation ($SmvO_2$) in NIRS examined tissue is shown by the equation:

$$SmvO_2 = Kv * SvO_2 + Ka * SaO_2 \qquad (\text{Eqn.4})$$

where "$SvO_2$" represents venous oxygen saturation; "$SaO_2$" represents arterial oxygen saturation; and Kv and Ka are the weighted venous and arterial contributions respectively, with Kv+Ka=1. The parameters Kv and Ka may have constant values, or they may be a function of $SvO_2$ and $SaO_2$. Determined oxygen saturation from the internal jugular vein ($SijvO_2$), jugular bulb ($SjbO_2$), or sagittal sinus ($SssO_2$) can be used to represent $SvO_2$. Therefore, the value of each term in Equation 4 is empirically determined, typically by discretely sampling or continuously monitoring and subsequently evaluating patient arterial and venous blood from tissue that the NIRS sensor is examining, and using regression analysis to determine the relative contributions of venous and arterial blood independent of the NIRS examination.

To non-invasively determine oxygen saturation within tissue at certain depth, it is necessary to limit the influence from the superficial tissues. For example, to determine brain oxygen saturation of adult human with NIRS technology, the contamination from extracranial tissue (scalp and skull) must be eliminated or limited.

What is needed, therefore, is a method for non-invasively determining the level of oxygen saturation within biological tissue that can determine the absolute oxygen saturation value rather than a change in level; a method that provides calibration means to account for energy losses (i.e. light attenuation) due to light scattering within tissue, other background absorption losses from biological compounds, and other unknown losses including measuring apparatus variability; and a method that can non-invasively determine oxygen saturation within tissue at certain depth by limiting the influence from the superficial tissues.

DISCLOSURE OF THE INVENTION

It is, therefore, an object of the present invention to provide a method for non-invasively determining the absolute oxygen saturation value within biological tissue.

It is a further object of the present invention to provide a method that provides calibration means to account for energy losses due to scattering as well as other background absorption from biological compounds.

It is a still further object of the present invention to provide a method that can non-invasively determine oxygen saturation within tissue at certain depth that limits the influence from the superficial tissues.

According to the present invention, a method and apparatus for non-invasively determining the blood oxygen saturation level within a subject's tissue is provided that utilizes a near infrared spectrophotometric (NIRS) sensor capable of transmitting a light signal into the tissue of a subject and sensing the light signal once it has passed through the tissue via transmittance or reflectance. The method includes the steps of: (1) transmitting a light signal into the subject's tissue, wherein the transmitted light signal includes a first wavelength, a second wavelength, and a third wavelength; (2) sensing a first intensity and a second intensity of the light signal, along the first, second, and third wavelengths after the light signal travels through the subject at a first and second predetermined distance; (3) determining an attenuation of the light signal for each of the first, second, and third wavelengths using the sensed first intensity and sensed second intensity of the first, second, and third wavelengths; (4) determining a difference in attenuation of the light signal between the first wavelength and the second wavelength, and between the first wavelength and the third wavelength; and (5) determining the blood oxygen saturation level within the subject's tissue using the difference in attenuation between the first wavelength and the second wavelength, and the difference in attenuation between the first wavelength and the third wavelength.

The present method makes it possible to account for energy losses (i.e. light attenuation) due to light scattering within tissue, other background absorption losses from biological compounds, and other unknown losses including measuring apparatus variability. By determining differential attenuation as a function of wavelength, the energy losses due to scattering as well as other background absorption from biological compounds are cancelled out or minimized relative to the attenuation attributable to deoxyhemoglobin, and attenuation attributable to oxyhemoglobin.

In order to account for the resulting minimized differential attenuation attributable to tissue light scattering characteristics, fixed light absorbing components, and measuring apparatus characteristics, each of the parameters must be measured or calibrated out. Since direct measurement is difficult, calibration to empirically determined data combined with data developed using the NIRS sensor is performed by using regression techniques. The empirically determined data is collected at or about the same time the data is developed with the NIRS sensor. Once the calibration parameters associated with attenuation attributable to tissue light scattering characteristics, fixed light absorbing components, and measuring apparatus characteristics have been determined, the NIRS sensor can be calibrated.

The calibrated sensor can then be used to accurately and non-invasively determine the total oxygen saturation level in the original subject tissue or other subject tissue. In addition, if effective pathlength of photon traveling through the tissue is known, for example, the separation distance ("d") between the light source to the light detector is known or is determinable, and the value of "$B_\lambda$", which represents the wavelength dependent light scattering differential pathlength factor, then the total amount of concentrations of deoxyhemoglobin (Hb) and oxyhemoglobin ($HbO_2$) within the examined tissue can be determined using the present method and apparatus.

The calibrated sensor can be used subsequently to calibrate similar sensors without having to invasively produce a blood sample. Hence, the present method and apparatus enables a non-invasive determination of the blood oxygen saturation level within tissue. For example, an operator can create reference values by sensing a light signal or other reference medium using the calibrated sensor. The operator can then calibrate an uncalibrated sensor by sensing the same light signal or reference medium, and subsequently adjusting the uncalibrated sensor into agreement with the calibrated sensor. Hence, once a reference sensor is created, other similar sensors can be calibrated without the need for invasive procedure.

There are, therefore, several advantages provided by the present method and apparatus. Those advantages include: 1) a practical non-invasive method and apparatus for determining oxygen saturation within tissue that can be used to determine the total blood oxygen saturation within tissue as opposed to a change in blood oxygen saturation; 2) a calibration method that accounts for energy losses (e.g., light attenuation) due to light scattering within tissue, other background absorption losses from biological compounds, and other unknown losses including measuring apparatus variability; 3) a practical non-invasive method and apparatus for determining oxygen saturation within tissue that can distinguish between the contribution of oxygen saturation attributable to venous blood and that saturation attributable to arterial blood; and 4) a practical non-invasive method and apparatus for determining oxygen saturation within tissue at certain depth that limits the influence from the superficial tissues.

In an alternative embodiment, aspects of the above-described methodology are combined with pulse oximetry techniques to provide a noninvasive method of distinguishing between blood oxygen saturation within tissue that is attributable to venous blood and that which is attributable to arterial blood. Pulse oximetry is used to determine arterial oxygen saturation, and the arterial oxygen saturation is, in turn, used to determine the venous oxygen saturation.

These and other objects, features, and advantages of the present invention method and apparatus will become apparent in light of the detailed description of the invention provided below and the accompanying drawings. The methodology and apparatus described below constitute a preferred embodiment of the underlying invention and do not, therefore, constitute all aspects of the invention that will or may become apparent by one of skill in the art after consideration of the invention disclosed overall herein.

DETAILED DESCRIPTION THE INVENTION

Figure 1:
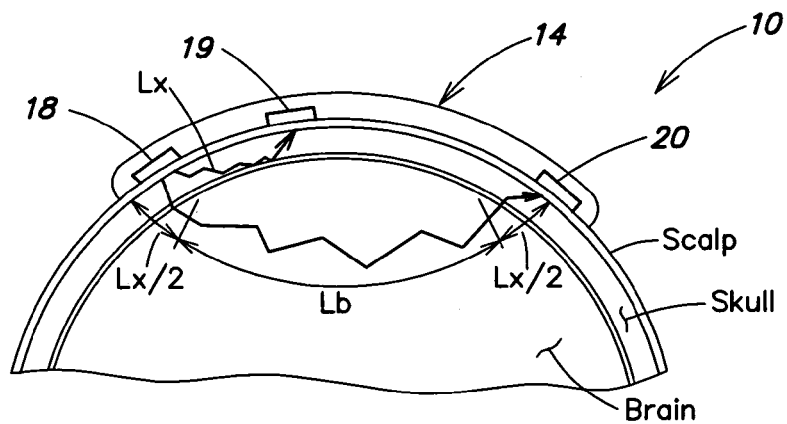
FIG. 1 is a diagrammatic representation of a NIRS sensor.
Figure 2:
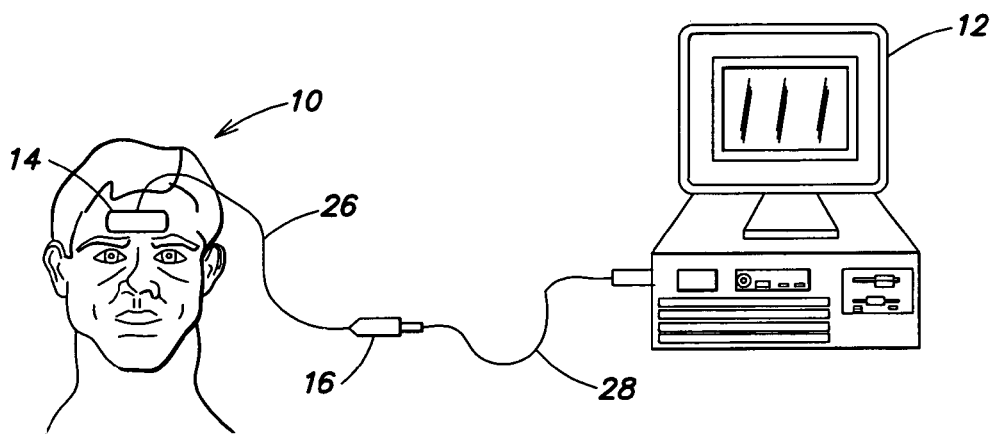
FIG. 2 is a diagrammatic representation of a NIRS sensor placed on a subject's head.
Figure 3:
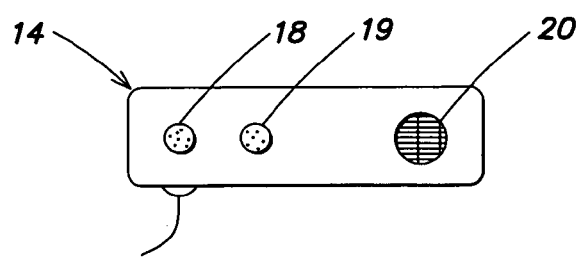
FIG. 3 is a diagrammatic view of a NIRS sensor.
Figure 4:
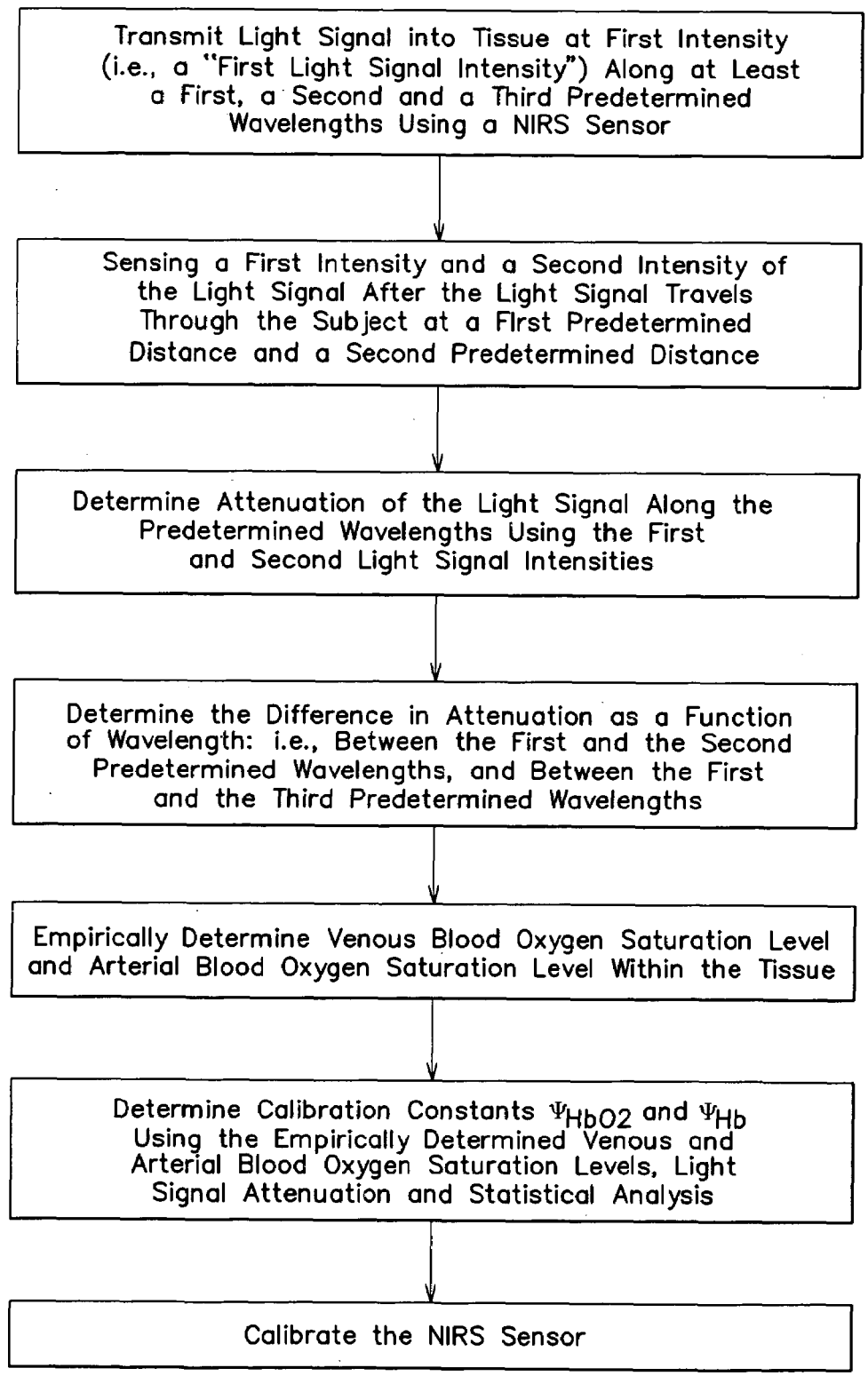
FIG. 4 is a block diagram of the present methodology for calibrating a NIRS sensor.
Figure 5:
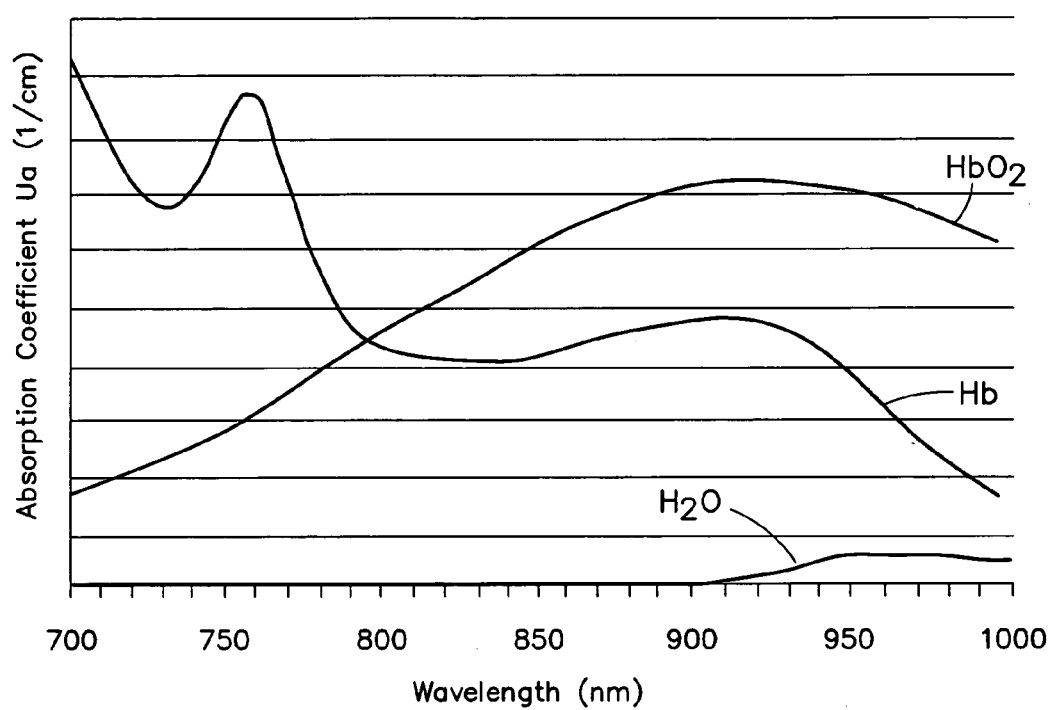
FIG. 5 is a graph showing an exemplary plot of absorption coefficient vs. wavelength.

The present method of and apparatus for non-invasively determining the blood oxygen saturation level within a subject's tissue is provided that utilizes a near infrared spectrophotometric (NIRS) sensor that includes a transducer capable of transmitting a light signal into the tissue of a subject and sensing the light signal once it has passed through the tissue via transmittance or reflectance. The present method and apparatus can be used with a variety of NIRS sensors. The present method is not limited to use with this preferred NIRS sensor, however.

Referring to FIGS. 1–5, the preferred NIRS sensor includes a transducer portion 10 and processor portion 12. The transducer portion 10 includes an assembly housing 14 and a connector housing 16. The assembly housing 14, which is a flexible structure that can be attached directly to a subject's body, includes one or more light sources 18 and light detectors 19, 20. A disposable adhesive envelope or pad is used for mounting the assembly housing 14 easily and securely to the subject's skin. Light signals of known but different wavelengths from the light sources 18 emit through a prism assembly 22. The light sources 18 are preferably laser diodes that emit light at a narrow spectral bandwidth at predetermined wavelengths. In one embodiment, the laser diodes are mounted within the connector housing 16. The laser diodes are optically interfaced with a fiber optic light guide to the prism assembly 22 that is disposed within the assembly housing 14. In a second embodiment, the light sources 18 are mounted within the assembly housing 14. A first connector cable 26 connects the assembly housing 14 to the connector housing 16 and a second connector cable 28 connects the connector housing 16 to the processor portion 12. The light detector 20 includes one or more photodiodes. The photodiodes are also operably connected to the processor portion 12 via the first and second connector cables 26, 28. The processor portion 12 includes a processor for processing light intensity signals from the light sources 18 and the light detectors 19, 20.

The processor utilizes an algorithm that characterizes a change in attenuation as a function of the difference in attenuation between different wavelengths. The present method advantageously accounts for but minimizes the effects of pathlength and parameter "E", which represent energy losses (i.e. light attenuation) due to light scattering within tissue (G), other background absorption losses from biological compounds (F), and other unknown losses including measuring apparatus variability (N). E=G+F+N.

Refer to FIG. 1, the absorption $A_{b\lambda}$ detected from the deep light detector 20 comprises attenuation and energy loss from both the deep and shallow tissue, while the absorption $A_{x\lambda}$ detected from the shallow light detector 19 comprises attenuation and energy loss from shallow tissue only.

Absorptions $A_{b\lambda}$ and $A_{x\lambda}$ can be expressed in the form of Equation 5 and Equation 6 below which is a modified version of Equation 2 that accounts for energy losses due to "E":

$$A_{b\lambda} = -\log(I_b/I_o)_\lambda = \alpha_\lambda * C_b * L_b + \alpha_\lambda * C_x * L_x + E_\lambda \quad \text{(Eqn. 5)}$$

$$A_{x\lambda} = -\log(I_x/I_o)_\lambda = \alpha_\lambda * C_x * L_x + E_{x\lambda} \quad \text{(Eqn. 6)}$$

Substituting Equation 6, into Equation 5 yields $A'_\lambda$, which represents attenuation and energy loss from deep tissue only:

$$A'_\lambda = A_{b\lambda} - A_{x\lambda} = \alpha_\lambda * C_b * L_b + (E_\lambda - E_{x\lambda}) = -\log\left(\frac{I_b}{I_x}\right)_\lambda \quad \text{(Eqn. 7)}$$

Where L is the effective pathlength of the photon traveling through the deep tissue and $A'_1$ and $A'_2$ are the absorptions of two different wavelengths. Let $E'_\lambda = E_\lambda - E_{x\lambda}$, therefore:

$$A_1' - A_2' = \Delta A_{12}' \quad \text{(Eqn. 8)}$$

Substituting Equation 7 into Equation 8 for $A'_1$ and $A'_2$, $\Delta A'_{12}$ can be expressed as:

$$\Delta A_{12}' = \alpha_{\lambda 12} * C_b * L_b + \Delta E_{12}' \quad \text{(Eqn. 9)}$$

and rewritten Equation 9 in expanded form:

$$\Delta A'_{12} = ((\alpha_{r1} - \alpha_{r2})[Hb]_b + (\alpha_{o1} - \alpha_{o2})[HbO_2]_b)L_b + (E'_1 - E'_2) \quad \text{(Eqn. 10)}$$
$$= (\Delta\alpha_{r12} * [Hb]_b * L_b) + (\Delta\alpha_{o12} * [HbO_2]_b * L_b) + \Delta E'_{12}$$

where:

$(\Delta\alpha_{r12} * [Hb]_b * L_b)$ represents the attenuation attributable to Hb;

$(\Delta\alpha_{o12} * [HbO_2]_b * L_b)$ represents the attenuation attributable to $HbO_2$; and $\Delta E_{12}'$ represents energy losses (i.e. light attenuation) due to light scattering within tissue, other background absorption losses from biological compounds, and other unknown losses including measuring apparatus variability.

The multivariate form of Equation 10 is used to determine $[HbO_2]_b$ and $[Hb]_b$ with three different wavelengths:

$$\begin{bmatrix} \Delta A'_{12} - \Delta E'_{12} \\ \Delta A'_{13} - \Delta E'_{13} \end{bmatrix}(L_b)^{-1} = \begin{bmatrix} \Delta\alpha_{r12} & \Delta\alpha_{o12} \\ \Delta\alpha_{r13} & \Delta\alpha_{o13} \end{bmatrix}\begin{bmatrix} [Hb]_b \\ [HbO_2]_b \end{bmatrix} \quad \text{(Eqn. 11)}$$

Rearranging and solving for $[HbO_2]_b$ and $[Hb]_b$, simplifying the $\Delta\alpha$ matrix into $[\Delta\alpha']$:

$$\begin{bmatrix} \Delta A'_{12} \\ \Delta A'_{13} \end{bmatrix}[\Delta\alpha']^{-1}(L_b)^{-1} - \begin{bmatrix} \Delta E'_{12} \\ \Delta E'_{13} \end{bmatrix}[\Delta\alpha']^{-1}(L_b)^{-1} = \begin{bmatrix} [Hb]_b \\ [HbO_2]_b \end{bmatrix} \quad \text{(Eqn. 12)}$$

Then combined matrices $[\Delta A'][\Delta\alpha']^{-1} = [A_c]$ and $[\Delta E][\Delta\alpha']^{-1} = [\Psi_c]$:

$$\begin{bmatrix} A_{Hb} \\ A_{HbO2} \end{bmatrix}(L_b)^{-1} - \begin{bmatrix} \Psi_{Hb} \\ \Psi_{HbO_2} \end{bmatrix}(L_b)^{-1} = \begin{bmatrix} [Hb]_b \\ [HbO_2]_b \end{bmatrix} \quad \text{(Eqn. 13)}$$

The parameters $A_{Hb}$ and $A_{HbO2}$ represent the product of the matrices $[(\Delta A_\lambda)]$ and $[\Delta\alpha']^{-1}$ and the parameters $\Psi_{Hb}$ and $\Psi_{HbO2}$ represent the product of the matrices $[\Delta E'_\lambda]$ and $[\Delta\alpha']^{-1}$. To determine the level of cerebral blood oxygen saturation ($SnO_2$), Equation 13 is rearranged using the form of Equation 1 and is expressed as follows:

$$SnO_2\% = \frac{(A_{HbO_2} - \Psi_{HbO_2})}{(A_{HbO_2} - \Psi_{HbO_2} + A_{Hb} - \Psi_{Hb})} * 100\% \quad \text{(Eqn. 14)}$$

Note that the effective pathlength $L_b$ cancels out in the manipulation from Equation 13 to Equation 14.

The value for $SnO_2$ is initially determined from $SmvO_2$ using Equation 4 and the empirically determined values for $SvO_2$ and $SaO_2$. The empirically determined values for $SvO_2$ and $SaO_2$ are based on data developed by discrete sampling or continuous monitoring of the subject's blood performed at or about the same time as the sensing of the tissue with the sensor. The temporal and physical proximity of the NIRS sensing and the development of the empirical data helps assure accuracy. The initial values for Kv and Ka within Equation 4 are clinically reasonable values for the circumstances at hand. The values for $A_{HbO2}$ and $A_{Hb}$ are determined mathematically using the values for $I_{b\lambda}$ and $I_{x\lambda}$ for each wavelength sensed with the NIRS sensor (e.g., using Equation 5 and 6). The calibration parameters $\Psi_{Hb}$ and $\Psi_{HbO2}$, which account for energy losses due to scattering as well as other background absorption from biological compounds, are then determined using Equation 14 and non-linear regression techniques by correlation to different weighted values of $SvO_2$ and $SaO_2$; i.e., different values of Ka and Kv. Statistically acceptable values of Kv and Ka and $\Psi_{Hb}$ and $\Psi_{HbO2}$ are converged upon using the non-linear regression techniques. Experimental findings show that after proper selection of Ka and Kv, the calibration parameters $\Psi_{Hb}$ and $\Psi_{HbO2}$ are constant within a statistically acceptable margin of error for an individual NIRS sensor used to monitor brain oxygenation on different human subjects. In other words, once the sensor is calibrated it can be used on various human subjects and produce accurate information for each human subject. The same is true for animal subjects.

In an alternative method of determining the absolute oxygen saturation value Equation 7 is rewritten:

$$A'_\lambda - E'_\lambda = \quad \text{(Eqn. 15)}$$
$$-\log\left(\frac{I_b}{I_x}\right)_\lambda - E'_\lambda = \alpha_\lambda * C * L_b = (\alpha_{r\lambda}[Hb]_b + \alpha_{o\lambda}[HbO_2]_b)L_b$$

For a two wavelength system, let "R" be a calibration index parameter:

$$R = \frac{A'_1 - E'_1}{A'_2 - E'_2} = \frac{(\alpha_{r1}[Hb]_b + \alpha_{o1}[HbO_2]_b)L_b}{(\alpha_{r2}[Hb]_b + \alpha_{o2}[HbO_2]_b)L_b} \quad \text{(Eqn. 16)}$$

-continued $$= \frac{\alpha_{r1} + \alpha_{o1}\frac{[HbO_2]_b}{[Hb]_b}}{\alpha_{r2} + \alpha_{o2}\frac{[HbO_2]_b}{[Hb]_b}} = \frac{\alpha_{r1} + \alpha_{o1}\frac{SnO_2}{1-SnO_2}}{\alpha_{r2} + \alpha_{o2}\frac{SnO_2}{1-SnO_2}}$$

Canceling out $L_b$ and substituting:

$$\frac{[HbO_2]_b}{[Hb]_b} = \frac{SnO_2}{1-SnO_2} \text{ form } SnO_2 = \frac{[HbO_2]_b}{[HbO_2]_b + [Hb]_b}$$

the following expression for $SnO_2$ is obtained:

$$SnO_2 = \frac{\alpha_{r1} - \alpha_{r2}R}{(\alpha_{r1} - \alpha_{o1}) + (\alpha_{r2} - \alpha_{r2})R} \quad \text{(Eqn. 17)}$$

The value of $A_1'$ and $A_2'$ are determined by measuring $I_b$ and $I_x$ for each wavelength. The parameters $E'_1$ and $E'_2$ can be considered as empirically determined calibration coefficients derived from the "best-fit" combinations of the weighted ratios of venous and arterial blood-oxygen saturation of the brain. By using non-linear regression techniques, the values of $E'_1$ and $E'_2$ are determined by correlating to different combinations of venous and arterial oxygen saturation weighted values to find the "best-fit" relationship of "R" as a function of $A_1'$, $A_2'$, $E'_1$ and $E'_2$ (Equation 17) to a specific ratio of venous and arterial saturation weighted values.

In the determination of the $SnO_2$ percentage, the effective photon pathlength $L_b$ cancels out. If, however, the photon pathlength is known or estimated, then the determination of the total value of Hb and/or $HbO_2$ is possible. For example, if a value for pathlength $L_b$ is input into Equation 13 along with the calibration values $\Psi_{Hb}$ and $\Psi_{HbO2}$, then the total value of Hb and/or $HbO_2$ can be calculated. According to Equation 2, pathlength L can be estimated from the product of "B*d". The light source to detector separation (optode) distance parameter "d" in the pathlength calculation is a measurable value and can be made constant by setting a fixed distance between light source to detector in the NIRS sensor design. Alternatively, the parameter "d" can be measured once the optodes are placed on the subject by use of calipers, ruler, or other distance measurement means. The pathiength differential factor "B" is more difficult LU measure and requires more sophisticated equipment. From a large data set of measured neonatal and adult head differential pathlength factor values, an estimation of the value of "B" can be determined within a statistically acceptable margin of error. Substitution of these predetermined values of "B" into Equation 13 results in the determination of the total values of Hb and $HbO_2$.

An alternative method of determining total values of Hb and $HbO_2$ combines Equation 3 and Equation 13 together. The multivariate form of Equation 3 is shown below:

$$\begin{bmatrix} -\log(I_{t2}/I_{t1})_{\lambda 1}/L_{\lambda 1} \\ -\log(I_{t2}/I_{t1})_{\lambda 2}/L_{\lambda 2} \\ -\log(I_{t2}/I_{t1})_{\lambda 3}/L_{\lambda 3} \end{bmatrix} = \begin{bmatrix} \alpha_{Hb\lambda 1} & \alpha_{HbO_2\lambda 1} \\ \alpha_{Hb\lambda 2} & \alpha_{HbO_2\lambda 2} \\ \alpha_{Hb\lambda 3} & \alpha_{HbO_2\lambda 3} \end{bmatrix} * \begin{bmatrix} \Delta Hb \\ \Delta HbO_2 \end{bmatrix} \quad \text{(Eqn. 18)}$$

At time $t=t_1$, the values of $\Delta Hb$ and $\Delta HbO_2$ are zero. Applying Equation 13, and knowing the calibration values of $\Psi_{Hb}$ and $\Psi_{HbO2}$ at a predetermined differential pathlength factor "B" and optode separation "d", the total absolute values of Hb and $HbO_2$ are determined at time $t=t_1$, which are represented by $[Hb]_{t1}$ and $[HbO_2]_{t1}$ respectively. At time $t=t_2$, the values of $\Delta Hb$ and $\Delta HbO_2$ are then determined using Equation 18. The total values of Hb and $HbO_2$ are then determined at time $t=t_2$ using the following equations:

$$[Hb]_{t2} = \Delta Hb(t_2) + [Hb]_{t1} \quad \text{(Eqn. 19)}$$

$$[HbO_2]_{t2} = \Delta HbO_2(t_2) + [HbO_2]_{t1} \quad \text{(Eqn. 20)}$$

Equations 19 and 20 are valid only if all the shared parameters in Equations 13 and 18 are exact. Reduced to practice, the advantage of combining Equations 13 and 18 result in improved signal to noise ratio (SNR) in the calculation of the total values for Hb and $HbO_2$. Conversely, improved SNR in the calculation of $SnO_2$ is also obtained from the following expression:

$$SnO_2\% = \frac{HbO_2}{HbO_2 + Hb} * 100\% \quad \text{(Eqn. 21)}$$

After the calibration parameters $\Psi_{Hb}$ and $\Psi_{HbO2}$ are determined using the above-described methodology for an individual NIRS sensor, this particular sensor is said to be calibrated. A calibrated NIRS sensor affords accurate measurement of total tissue oxygen saturation, $SnO_2$, by non-invasive means. The calibrated sensor can be used thereafter on any human patient, including adults and neonates. The same is true for animal subject if the sensor was calibrated on animals. Although the present method is described above in terms of sensing blood oxygenation within cerebral tissue, the present method and apparatus are not limited to cerebral applications and can be used to determine blood oxygenation within tissue found elsewhere within the subject's body.

According to an additional aspect of the present invention, the above-described method can also be used to establish a calibrated "reference" sensor that can be used to calibrate similar sensors through the use of a phantom sample (also referred to as a "reference sample"). The phantom sample has optical characteristics that are similar to the tissue being examined by the NIRS sensor. The calibrated reference NIRS sensor is used to sense the phantom sample and produce reference values. Similar, but uncalibrated, NIRS sensors can thereafter be calibrated by sensing the same phantom sample and adjusting either the hardware of the uncalibrated sensor or the output of the uncalibrated sensor until the output of the uncalibrated sensor agrees with the reference values produced by the calibrated reference sensor. Therefore, the calibration parameters $\Psi_{Hb}$ and $\Psi_{HbO2}$ for the uncalibrated sensor would be determined from the phantom sample. This technique makes it unnecessary to calibrate each new sensor in the manner described above, and thereby provides a relatively quick and cost effective way to calibrate NIRS sensors.

Besides Hb and $HbO_2$, other biological constituents of interest (e.g., cytochrome $aa_3$, etc.) could be determined using the multivariate forms of equations 2, 3, 6 or 7. For each additional constituent to be determined, an additional measuring wavelength will be needed.

In an alternative embodiment, the above-described methodology can be combined with pulse oximetry techniques to provide an alternative noninvasive method of distinguishing between oxygen saturation attributable to venous blood and that attributable to arterial blood. As demonstrated by Equation 4, $SmvO_2$ is determined by the ratio of venous oxygen saturation $SvO_2$ and arterial oxygen saturation $SaO_2$. A calibrated NIRS sensor affords accurate measurement of total tissue oxygen saturation, $SnO_2$, by using regression techniques by correlation to mixed venous oxygen saturation $SmvO_2$. Therefore, the following expression will result:

$$SnO_2 = SmvO_2 = K_v * SvO_2 + Ka * SaO_2 \quad \text{(Eqn. 22)}$$

Non-invasive pulse oximetry techniques can be used to determine the arterial oxygen saturation ($SaO_2$) of peripheral tissue (i.e. finger, ear, nose) by monitoring pulsatile optical attenuation changes of detected light induced by pulsatile arterial blood volume changes in the arteriolar vascular system. Arterial blood oxygen saturation determined by pulse oximetry is clinically denoted as $SpO_2$. If NIRS monitoring and pulse oximetry monitoring are done simultaneously and $SpO_2$ is set equal to $SaO_2$ in Equation 23, then venous oxygen saturation can be determined from the following expression:

$$SvO_2 = \frac{SnO_2 - (Ka * SpO_2)}{Kv} \quad \text{(Eqn. 23)}$$

For the brain, venous oxygen saturation $SvO_2$ would be determined from internal jugular vein ($SijvO_2$), jugular bulb ($SjbO_2$), or sagittal sinus ($SssO_2$) and the parameters Ka and Kv would be empirically determined during the calibration of the NIRS sensor. Under most physioloqical conditions, $SpO_2$ is representative of brain arterial oxygen saturation $SaO_2$. Therefore, depending on which venous saturation parameter was used to calibrate the NIRS sensor, this clinically important parameter (i.e., $SijvO_2$, $SjbO_2$, or $SssO_2$) can be determined by Equation 24 by non-invasive means.

Since many changes and variations of the disclosed embodiment of the invention may be made without departing from the inventive concept, it is not intended to limit the invention otherwise than as required by the appended claims.

The invention claimed is:

1. A method for non-invasively determining a blood oxygen saturation level within a subject's tissue using a near infrared spectrophotometric sensor, said method comprising the steps of:
transmitting a light signal into the subject's tissue using the sensor, wherein the transmitted light signal includes a first wavelength, a second wavelength, and a third wavelength;
sensing a first intensity and a second intensity of the light signal, using the sensor, along the first, second, and third wavelengths after the light signal travels through the subject at a first predetermined distance and a second predetermined distance;
wherein the sensor is calibrated using empirical data that relates to the subject's tissue that is sensed by the sensor to account for light signal attenuation resulting from light signal scattering within the subject's tissue;
determining an attenuation of the light signal for each of the first, second, and third wavelengths using the sensed first intensity and sensed second intensity of the first, second, and third wavelengths;
determining a difference in attenuation of the light signal between the first wavelength and the second wavelength, and between the first wavelength and the third wavelength;
determining the blood oxygen saturation level within the subject's tissue using the difference in attenuation between the first wavelength and the second wavelength, and the difference in attenuation between the first wavelength and the third wavelength.

2. The method of claim 1, wherein the sensor is calibrated using the equation:

$$SmvO_2 = Kv * SvO_2 + Ka * SaO_2.$$

3. The method of claim 2, wherein the sensor is calibrated by using empirical data to determine a first calibration constant and a second calibration constant.

4. The method of claim 3, wherein the step of determining the blood oxygen saturation level within the subject's tissue utilizes the equation:

$$Sn\,O_2\,\% = \frac{(A_{HbO_2} - \Psi_{HbO_2})}{(A_{HbO_2} - \Psi_{HbO_2} + A_{Hb} - \Psi_{Hb})} * 100\,\%$$

where $\Psi_{HbO_2}$ represents the first calibration constant, $\Psi_{Hb}$ represents the second calibration constant, $A_{HbO_2}$ represents a difference in attenuation of light signal attributable to oxyhemoglobin, and $A_{Hb}$ represents a difference in attenuation of light signal attributable to deoxyhemoglobin.

5. The method of claim 4, further comprising the steps of:
determining a photon pathlength $L_b$; and
determining a concentration of oxyhemoglobin and a concentration of deoxyhemoglobin within the subject's tissue using the first and second calibration constants.

6. The method of claim 5, wherein the concentration of oxyhemoglobin and the concentration of deoxyhemoglobin within the subject's tissue are determined using the equation:

$$\begin{bmatrix} A_{Hb} \\ A_{HbO_2} \end{bmatrix}(L_b)^{-1} - \begin{bmatrix} \Psi_{Hb} \\ \Psi_{HbO_2} \end{bmatrix}(L_b)^{-1} = \begin{bmatrix} [Hb]_b \\ [HbO_2]_b \end{bmatrix}.$$

7. The method of claim 6, wherein the step of determining a difference in attenuation of the light signal between the first wavelength and the second wavelength utilizes the equation:

$$\Delta A'_{12} = A'_1 - A'_2 = -\log(I_b/I_x)_1 + \log(I_b/I_x)_2$$
$$= \{(\alpha_{r1} - \alpha_{r2})[Hb]_b + (\alpha_{o1} - \alpha_{o2})[HbO_2]_b\}L_b + (E'_1 - E'_2)$$
$$= (\Delta\alpha_{r12}[Hb]_b + \Delta\alpha_{o12}[HbO_2]_b)L_b + \Delta E_{12}$$

and the step of determining a difference in attenuation of the light signal between the first wavelength and the third wavelength utilizes the equation:

$$\Delta A'_{13} = A'_1 - A'_3 = -\log(I_b/I_x)_1 + \log(I_b/I_x)_3$$
$$= \{(\alpha_{r1} - \alpha_{r3})[Hb]_b + (\alpha_{o1} - \alpha_{o3})[HbO_2]_b\}L_b + (E'_1 - E'_3)$$
$$= (\Delta\alpha_{r13}[Hb]_b + \Delta\alpha_{o13}[HbO_2]_b)L_b + \Delta E_{13}.$$

8. The method of claim 7, wherein the step of determining an attenuation of the light signal utilizes the equation:

$$A'_\lambda = -\log(I_b/I_x)_\lambda = (\alpha_{r\lambda}[Hb]_b + \alpha_{o1\lambda}[HbO_2]_b)L_b + E'_\lambda$$
$$= (\alpha_{r\lambda}[Hb]_b + \alpha_{o\lambda}[HbO_2]_b)L_b + (E - E_x)_\lambda$$

for one or more of the first, second, and third wavelengths.

9. The method of claim 1, wherein the step of determining a difference in attenuation of the light signal between the first wavelength and the second wavelength utilizes the equation:

$$\Delta A'_{12} = A'_1 - A'_2 = -\log(I_b/I_x)_1 + \log(I_b/I_x)_2$$
$$= \{(\alpha_{r1} - \alpha_{r2})[Hb]_b + (\alpha_{o1} - \alpha_{o2})[HbO_2]_b\}L_b + (E'_1 - E'_2)$$
$$= (\Delta\alpha_{r12}[Hb]_b + \Delta\alpha_{o12}[HbO_2]_b)L_b + \Delta E_{12}$$

and the step of determining a difference in attenuation of the light signal between the first wavelength and the third wavelength utilizes the equation:

$$\Delta A'_{13} = A'_1 - A'_3 = -\log(I_b/I_x)_1 + \log(I_b/I_x)_3$$
$$= \{(\alpha_{r1} - \alpha_{r3})[Hb]_b + (\alpha_{o1} - \alpha_{o3})[HbO_2]_b\}L_b + (E'_1 - E'_3)$$
$$= (\Delta\alpha_{r13}[Hb]_b + \Delta\alpha_{o13}[HbO_2]_b)L_b + \Delta E_{13}.$$

10. The method of claim 9, wherein the step of determining an attenuation of the light signal of a wavelength $\lambda$ utilizes the equation:

$$A'_\lambda = -\log(I_b/I_x)_\lambda = (\alpha_{r\lambda}[Hb]_b + \alpha_{o\lambda}[HbO_2]_b)L'_b + E'_\lambda$$
$$= (\alpha_{r\lambda}[Hb]_b + \alpha_{o\lambda}[Hbo_2]_b)L_b + (E - E_x)_\lambda.$$

11. A method for determining a blood oxygen saturation level within a subject's tissue using a near infrared spectrophotometric sensor attached to the skin of the subject, said method comprising the steps of:

transmitting a light signal into the subject's tissue, wherein the transmitted light signal includes a first wavelength, a second wavelength, and a third wavelength;

sensing a first intensity and a second intensity of the light signal, using the sensor, along the first, second, and third wavelengths after the light signal travels through the subject at a first predetermined distance and a second predetermined distance;

determining an attenuation of the light signal for each of the first, second, and third wavelengths using the first intensity and the sensed second intensity of the first, second, and third wavelengths;

determining a difference in attenuation of the light signal between the first wavelength and the second wavelength, and between the first wavelength and the third wavelength;

determining a first calibration constant and a second calibration constant using empirical data developed from the subject at or about the same time as when the sensing occurs;

determining the blood oxygen saturation level within the subject's tissue using the difference in attenuation between the first wavelength and the second wavelength, and the difference in attenuation between the first wavelength and the third wavelength, and the first calibration constant and the second calibration constant.

12. The method of claim 11 wherein the empirical data is collected by discretely sampling a venous blood source and an arterial blood source from the subject.

13. The method of claim 11 wherein the empirical data is collected by continuously monitoring a venous blood source and an arterial blood source from the subject.

14. The method of claim 11, wherein the sensor is calibrated using the equation:

$$SmvO_2 = Kv*SvO_2 + Ka*SaO_2.$$

15. The method of claim 14, wherein the step of determining the blood oxygen saturation level within the subject's tissue utilizes the equation:

$$SnO_2\% = \frac{(A_{HbO_2} - \Psi_{HbO_2})}{(A_{HbO_2} - \Psi_{HbO_2} + A_{Hb} - \Psi_{Hb})} * 100\%$$

where $\Psi_{HbO2}$ represents the first calibration constant, $\Psi_{Hb}$ represents the second calibration constant, $A_{HbO2}$ represents a difference in attenuation of light signal attributable to oxyhemoglobin, and $A_{Hb}$ represents a difference in attenuation of light signal attributable to deoxyhemoglobin.

16. The method of claim 15, further comprising the steps of:

determining a photon pathlength $L_b$; and determining the concentration of oxyhemoglobin and deoxyhemoglobin within the subject's tissue using the first and second calibration constants.

17. The method of claim 16, wherein the concentration of oxyhemoglobin and deoxyhemoglobin within the subject's tissue are determined using the equation:

$$\begin{bmatrix} A_{Hb} \\ A_{HbO_2} \end{bmatrix}(L_b)^{-1} - \begin{bmatrix} \Psi_{Hb} \\ \Psi_{HbO_2} \end{bmatrix}(L_b)^{-1} = \begin{bmatrix} Hb \\ HbO_2 \end{bmatrix}.$$

18. The method of claim 17, wherein the step of determining a difference in attenuation of the light signal between the first wavelength and the second wavelength utilizes the equation:

$$\Delta A'_{12} = A'_1 - A'_2 = -\log\left(\frac{I_b}{I_x}\right)_1 + \log\left(\frac{I_b}{I_x}\right)_2 =$$

-continued
$$\{(\alpha_{r1} - \alpha_{r2})[Hb]_b + (\alpha_{o1} - \alpha_{o2})[HbO_2]_b\}L_b + (E'_1 - E'_2) =$$
$$(\Delta\alpha_{r12}[Hb]_b + \Delta\alpha_{o12}[HbO_2]_b)L_b + \Delta E_{12}$$

and the step of determining a difference in attenuation of the light signal between the first wavelength and the third wavelength utilizes the equation:

$$\Delta A'_{13} = A'_1 - A'_3 = -\log\left(\frac{I_b}{I_x}\right)_1 + \log\left(\frac{I_b}{I_x}\right)_3 =$$
$$\{(\alpha_{r1} - \alpha_{r3})[Hb]_b + (\alpha_{o1} - \alpha_{o3})[HbO_2]_b\}L_b + (E'_1 - E'_3) =$$
$$(\Delta\alpha_{r13}[Hb]_b + \Delta\alpha_{o13}[HbO_2]_b)L_b + \Delta E_{13}.$$

19. The method of claim 18, wherein the step of determining an attenuation of the light signal utilizes the equation:

$$A'_\lambda = -\log(I_b/I_x)_\lambda = (\alpha_{r\lambda}[Hb]_b + \alpha_{o\lambda}[HbO_2]_b)L_b + E'_\lambda$$
$$= (\alpha_{r\lambda}[Hb]_b + \alpha_{o\lambda}[HbO_2]_b)L_b + (E - E_x)_\lambda$$

for one or more of the first, second, and third wavelengths.

20. The method of claim 11, wherein the step of determining a difference in attenuation of the light signal between the first wavelength and the second wavelength utilizes the equation:

$$\Delta A'_{12} = A'_1 - A'_2 = -\log\left(\frac{I_b}{I_x}\right)_1 + \log\left(\frac{I_b}{I_x}\right)_2 =$$
$$\{(\alpha_{r1} - \alpha_{r2})[Hb]_b + (\alpha_{o1} - \alpha_{o2})[HbO_2]_b\}L_b + (E'_1 - E'_2) =$$
$$(\Delta\alpha_{r12}[Hb]_b + \Delta\alpha_{o12}[HbO_2]_b)L_b + \Delta E_{12}$$

and the step of determining a difference in attenuation of the light signal between the first wavelength and the third wavelength utilizes the equation:

$$\Delta A'_{13} = A'_1 - A'_3 = -\log\left(\frac{I_b}{I_x}\right)_1 + \log\left(\frac{I_b}{I_x}\right)_3 =$$
$$\{(\alpha_{r1} - \alpha_{r3})[Hb]_b + (\alpha_{o1} - \alpha_{o3})[HbO_2]_b\}L_b + (E'_1 - E'_3) =$$
$$(\Delta\alpha_{r13}[Hb]_b + \Delta\alpha_{o13}[HbO_2]_b)L_b + \Delta E_{13}.$$

21. The method of claim 20, wherein the step of determining a attenuation of the light signal utilizes the equation:

$$A'_\lambda = -\log(I_b/I_x)_\lambda = (\alpha_{r\lambda}[Hb]_b + \alpha_{o\lambda}[HbO_2]_b)L_b + E'_\lambda$$
$$= (\alpha_{r\lambda}[Hb]_b + \alpha_{o\lambda}[HbO_2]_b)L_b + (E - E_x)_\lambda$$

for one or more of the first, second, and third wavelengths.

22. The method of claim 11, wherein the step of determining the blood oxygen saturation level within the subject's tissue utilizes the equation:

$$SnO_2\% = \frac{(A_{HbO_2} - \Psi_{HbO_2})}{(A_{HbO_2} - \Psi_{HbO_2} + A_{Hb} - \Psi_{Hb})} * 100\%$$

where $\Psi_{HbO_2}$ represents the first calibration constant, $\Psi_{Hb}$ represents the second calibration constant, $A_{HbO_2}$ represents a difference in attenuation of light signal attributable to oxyhemoglobin, and $A_{Hb}$ represents a difference in attenuation of light signal attributable to deoxyhemoglobin.

23. The method of claim 22, further comprising the steps of:
  determining a photon pathlength $L_b$, and
  determining the concentration of oxyhemoglobin and deoxyhemoglobin within the subject's tissue using the first and second calibration constants.

24. The method of claim 23, wherein the concentration of oxyhemoglobin and deoxyhemoglobin within the subject's tissue are determined using the equation:

$$\begin{bmatrix} A_{Hb} \\ A_{HbO_2} \end{bmatrix}(L_b)^{-1} - \begin{bmatrix} \Psi_{Hb} \\ \Psi_{HbO_2} \end{bmatrix}(L_b)^{-1} = \begin{bmatrix} Hb \\ HbO_2 \end{bmatrix}.$$

25. The method of claim 24, wherein the step of determining a difference in attenuation of the light signal between the first wavelength and the second wavelength utilizes the equation:

$$\Delta A'_{12} = A'_1 - A'_2 = -\log\left(\frac{I_b}{I_x}\right)_1 + \log\left(\frac{I_b}{I_x}\right)_2 =$$
$$\{(\alpha_{r1} - \alpha_{r2})[Hb]_b + (\alpha_{o1} - \alpha_{o2})[HbO_2]_b\}L_b + (E'_1 - E'_2) =$$
$$(\Delta\alpha_{r12}[Hb]_b + \Delta\alpha_{o12}[HbO_2]_b)L_b + \Delta E_{12}$$

and the step of determining a difference in attenuation of the light signal between the first wavelength and the third wavelength utilizes the equation:

$$\Delta A'_{13} = A'_1 - A'_3 = -\log\left(\frac{I_b}{I_x}\right)_1 + \log\left(\frac{I_b}{I_x}\right)_3 =$$
$$\{(\alpha_{r1} - \alpha_{r3})[Hb]_b + (\alpha_{o1} - \alpha_{o3})[HbO_2]_b\}L_b + (E'_1 - E'_3) =$$
$$(\Delta\alpha_{r13}[Hb]_b + \Delta\alpha_{o13}[HbO_2]_b)L_b + \Delta E_{13}.$$

26. The method of claim 25, wherein the step of determining an attenuation of the light signal utilizes the equation:

$$A'_\lambda = -\log(I_b/I_x)_\lambda = (\alpha_{r\lambda}[Hb]_b + \alpha_{o\lambda}[HbO_2]_b)L_b + E'_\lambda$$
$$= (\alpha_{r\lambda}[Hb]_b + \alpha_{o\lambda}[HbO_2]_b)L_b + (E - E_x)_\lambda$$

for one or more of the first, second, and third wavelengths.

27. A method for calibrating a near infrared spectrophotometric sensor for use in determining the blood oxygen saturation level within a subject's tissue, said method comprising the steps of:

transmitting a light signal into the subject's tissue, wherein the transmitted light signal includes a first wavelength, a second wavelength, and a third wavelength;

sensing a first intensity and a second intensity of the light signal, using the sensor, along the first, second, and third wavelengths after the light signal travels through the subject at a first and second predetermined distances;

determining an attenuation of the light signal for each of the first, second, and third wavelengths using the first intensity and the sensed second intensity of the first, second, and third wavelengths;

determining a difference in attenuation of the light signal between the first wavelength and the second wavelength, and between the first wavelength and the third wavelength;

determining a first calibration constant and a second calibration constant using empirical data developed from the subject at or about the same time as when the sensing occurs; and calibrating the sensor using the first calibration constant and the second calibration constant.

28. The method of claim 27, wherein the empirical data is collected by discretely sampling a venous blood source and an arterial blood source from the subject.

29. The method of claim 27, wherein the empirical data is collected by continuously monitoring a venous blood source and an arterial blood source from the subject.

30. The method of claim 27, wherein the sensor is calibrated using the equation:

$$SmvO_2 = Kv * SvO_2 + Ka * SaO_2.$$

31. The method of claim 27, wherein the step of determining a difference in attenuation of the light signal between the first wavelength and the second wavelength utilizes the equation:

$$\Delta A'_{12} = A'_{\lambda 1} - A'_{\lambda 2} = -\log\left(\frac{I_b}{I_x}\right)_1 + \log\left(\frac{I_b}{I_x}\right)_2 =$$
$$\{(\alpha_{r1} - \alpha_{r2})[Hb]_b + (\alpha_{o1} - \alpha_{o2})[HbO_2]_b\}L_b + (E'_1 - E'_2) =$$
$$(\Delta\alpha_{r12}[Hb]_b + \Delta\alpha_{o12}[HbO_2]_b)L_b + \Delta E_{12}$$

and the step of determining a difference in attenuation of the light signal between the first wavelength and the third wavelength utilizes the equation:

$$\Delta A'_{13} = A'_{\lambda 1} - A'_{\lambda 3} = -\log\left(\frac{I_b}{I_x}\right)_1 + \log\left(\frac{I_b}{I_x}\right)_3 =$$
$$\{(\alpha_{r1} - \alpha_{r3})[Hb]_b + (\alpha_{o1} - \alpha_{o3})[HbO_2]_b\}L_b + (E'_1 - E'_3) =$$
$$(\Delta\alpha_{r13}[Hb]_b + \Delta\alpha_{o13}[HbO_2]_b)L_b + \Delta E_{13}.$$

32. The method of claim 31, wherein the step of determining an attenuation of the light signal utilizes the equation:

$$A'_\lambda = -\log(I_b/I_x)_\lambda = (\alpha_{r\lambda}[Hb]_b + \alpha_{o\lambda}[HbO_2]_b)L_b + E'_\lambda .$$
$$= (\alpha_{r\lambda}[Hb]_b + \alpha_{o\lambda}[HbO_2]_b)L_b + (E - E_x)_\lambda$$

for one or more of the first, second, and third wavelengths.

33. A method for calibrating a NIRS sensor, said method comprising the steps of:

transmitting a first light signal from a calibrated NIRS sensor into a reference sample, wherein the transmitted first light signal includes a first wavelength, a second wavelength, and a third wavelength;

sensing a first intensity and a second intensity of the first light signal with the calibrated NIRS sensor along the first, second, and third wavelengths after the first light signal travels through the reference sample;

determining a first attenuation of the first light signal for each of the first, second, and third wavelengths using the first intensity and the second intensity of the first light signal sensed with the calibrated NIRS sensor;

transmitting a second light signal from an uncalibrated second NIRS sensor into the reference sample at a predetermined first intensity, wherein the transmitted second light signal includes a first wavelength, a second wavelength, and a third wavelength;

sensing a second intensity of the second light signal with the uncalibrated second NIRS sensor along the first, second, and third wavelengths after the second light signal travels through the subject;

determining a second attenuation of the second light signal for each of the first, second, and third wavelengths using the predetermined first intensity and the second intensity of the first, second, and third wavelengths sensed with the uncalibrated second NIRS sensor;

adjusting the uncalibrated second NIRS sensor so that the second attenuation substantially agrees with the first attenuation.

34. A method for non-invasively determining a concentration of oxyhemoglobin and a concentration of deoxyhemoglobin within a subject's tissue using a near infrared spectrophotometric sensor, said method comprising the steps of:

(a) determining a blood oxygen saturation level with the subject's tissue by transmitting a light signal into the subject's tissue from a NIRS sensor, wherein the transmitted light signal includes a first wavelength, a second wavelength, and a third wavelength;

sensing a first intensity and a second intensity of the light signal, using the sensor, along the first, second, and third wavelengths after the light signal travels through the subject at a first and second predetermined distances;

wherein the sensor is calibrated using empirical data that relates to the subject's tissue that is sensed by the sensor to account for light signal attenuation resulting from light signal scattering within the subject's tissue;

determining an attenuation of the light signal for each of the first, second, and third wavelengths using the first intensity and the sensed second intensity of the first, second, and third wavelengths;

determining a difference in attenuation of the light signal between the first wavelength and the second wavelength, and between the first wavelength and the third wavelength;

determining a first calibration constant and a second calibration constant using empirical data developed from the subject at or about the same time as when the sensing occurs;

determining the blood oxygen saturation level within the subject's tissue using the difference in attenuation between the first wavelength and the second wavelength, and the difference in attenuation between the first wavelength and the third wavelength, and the first calibration constant and the second calibration constant;

(b) determining a photon pathlength $L_b$, and (c) determining the concentration of oxyhemoglobin and the concentration of deoxyhemoglobin within the subject's tissue using the first and second calibration constants.

35. The method of claim 34, wherein the concentration of oxyhemoglobin and the concentration of deoxyhemoglobin within the subject's tissue are determined using the equation:

$$\begin{bmatrix} A_{Hb} \\ A_{HbO_2} \end{bmatrix}(L_b)^{-1} - \begin{bmatrix} \Psi_{Hb} \\ \Psi_{HbO_2} \end{bmatrix}(L_b)^{-1} = \begin{bmatrix} Hb \\ HbO_2 \end{bmatrix}$$

where $\Psi_{HbO_2}$ represents the first calibration constant, $\Psi_{Hb}$ represents the second calibration constant, $A_{HbO_2}$ represents a difference in attenuation of light signal attributable to oxyhemoglobin, and $A_{Hb}$ represents a difference in attenuation of light signal attributable to deoxyhemoglobin.

36. A method for non-invasively determining a concentration of oxyhemoglobin and a concentration of deoxyhemoglobin within a subject's tissue at an initial time t1 and a subsequent time t2 using a near infrared spectrophotometric sensor, said method comprising the steps of:

(a) determining a blood oxygen saturation level with the subject's tissue by transmitting a light signal into the subject's tissue from a NIRS sensor, wherein the transmitted light signal includes a first wavelength, a second wavelength, and a third wavelength;

sensing a first intensity and a second intensity of the light signal, using the sensor, along the first, second, and third wavelengths after the light signal travels through the subject at a first and second predetermined distances;

wherein the sensor is calibrated using empirical data that relates to the subject's tissue that is sensed by the sensor to account for light signal attenuation resulting from light signal scattering within the subject's tissue;

determining an attenuation of the light signal for each of the first, second, and third wavelengths using the first intensity and the sensed second intensity of the first, second, and third wavelengths;

determining a difference in attenuation of the light signal between the first wavelength and the second wavelength, and between the first wavelength and the third wavelength;

determining a first calibration constant and a second calibration constant using empirical data developed from the subject at or about the same time as when the sensing occurs;

determining the blood oxygen saturation level within the subject's tissue using the difference in attenuation between the first wavelength and the second wavelength, and the difference in attenuation between the first wavelength and the third wavelength, and the first calibration constant and the second calibration constant;

(b) determining a photon pathlength $L_b$;

(c) determining the concentration of oxyhemoglobin and the concentration of deoxyhemoglobin within the subject's tissue at the initial time t1 using the equation:

$$\begin{bmatrix} A_{Hb} \\ A_{HbO_2} \end{bmatrix}(L_b)^{-1} - \begin{bmatrix} \Psi_{Hb} \\ \Psi_{HbO_2} \end{bmatrix}(L_b)^{-1} = \begin{bmatrix} Hb \\ HbO_2 \end{bmatrix}$$

where $\Psi_{HbO_2}$ represents the first calibration constant, $\Psi_{Hb}$ represents the second calibration constant, $A_{HbO_2}$ represents a difference in attenuation of light signal attributable to oxyhemoglobin, and $A_{Hb}$ represents a difference in attenuation of light signal attributable to deoxyhemoglobin; and (d) determining a change in the concentration of oxyhemoglobin and a change in the concentration of deoxyhemoglobin from the initial time t1 to a subsequent second time t2, determined using the equation:

$$\begin{bmatrix} -\log\left(\frac{I_{t2}}{I_{t1}}\right)_{\lambda 1}/L_{\lambda 1} \\ -\log\left(\frac{I_{t2}}{I_{t1}}\right)_{\lambda 2}/L_{\lambda 2} \\ -\log\left(\frac{I_{t2}}{I_{t1}}\right)_{\lambda 3}/L_{\lambda 3} \end{bmatrix} = \begin{bmatrix} \alpha_{Hb\lambda 1} & \alpha_{HbO_2 \lambda 1} \\ \alpha_{Hb\lambda 2} & \alpha_{HbO_2 \lambda 2} \\ \alpha_{Hb\lambda 3} & \alpha_{HbO_2 \lambda 3} \end{bmatrix} * \begin{bmatrix} \Delta Hb \\ \Delta HbO_2 \end{bmatrix}$$

; and (e) determining the concentration of oxyhemoglobin and the concentration of deoxyhemoglobin within the subject's tissue at the subsequent time t2 using the equations:

$[Hb]_{t_2} = \Delta Hb(t_2) + [Hb]_{t_1}$ and $[HbO_2]_{t_2} = \Delta HbO_2(t_2) + [HbO_2]_{t_1}$.

37. A method for non-invasively determining a blood oxygen saturation level within a subject's tissue using a near infrared spectrophotometric sensor, said method comprising the steps of:

transmitting a light signal into the subject's tissue using the sensor;

sensing a first intensity and a second intensity of the light signal, using the sensor, along three or more selectively chosen wavelengths after the light signal travels through the subject at a first and second predetermined distances;

wherein the sensor is calibrated using empirical data that relates to the subject's tissue that is sensed by the sensor to account for light signal attenuation resulting from light signal scattering within the subject's tissue;

determining an attenuation of the light signal for at least "n" number of the selectively chosen wavelengths using the first intensity and the sensed second intensity of the selectively chosen wavelengths, where "n" is an integer equal to or greater than three;

determining a difference in attenuation of the light signal between a first wavelength and each of "n" number of the selectively chosen wavelengths;

determining the blood oxygen saturation level within the subject's tissue using the difference in attenuation between the first wavelength and each of the "n" number of other selectively chosen wavelengths.

38. A method for determining a blood oxygen saturation level within a subject's tissue using a near infrared spectrophotometric sensor attached to the skin of the subject, said method comprising the steps of:
   transmitting a light signal into the subject's tissue;
   sensing a first intensity and a second intensity of the light signal, using the sensor, along three or more selectively chosen wavelengths after the light signal travels through the subject at a first and second predetermined distances;
   determining an attenuation of the light signal for at least "n" number of the selectively chosen wavelengths using the first intensity and the sensed second intensity of the selectively chosen wavelengths, where "n" is an integer equal to or greater than three;
   determining a difference in attenuation of the light signal between a first wavelength and each of "n" number of the selectively chosen wavelengths;
   determining a first calibration constant and a second calibration constant using empirical data developed from the subject at or about the same time as when the sensing occurs;
   determining the blood oxygen saturation level within the subject's tissue using the difference in attenuation between the first wavelength and each of "n" number of the selectively chosen wavelengths, and the first calibration constant and the second calibration constant.

39. A method for non-invasively determining a blood oxygen saturation level within a subject's tissue using a near infrared spectrophotometric sensor, said method comprising the steps of:
   transmitting a light signal into the subject's tissue using the sensor, wherein the transmitted light signal includes a first wavelength, and a second wavelength;
   sensing a first intensity and a second intensity of the light signal, using the sensor, along the first wavelength, after the light signal travels through the subject at a first and a second predetermined distances;
   sensing a third intensity and a fourth intensity of the light signal, using the sensor, along the second wavelength, after the light signal travels through the subject at said first and said second predetermined distances;
   wherein the sensor is calibrated using empirical data that relates to the subject's tissue that is sensed by the sensor to account for light signal attenuation resulting from light signal scattering within the subject's tissue;
   determining a first attenuation of the light signal for the first wavelength using said first intensity and said second intensity;
   determining a second attenuation of the light signal for the second wavelength using said third intensity and said fourth intensity;
   determining a ratio of said first and said second attenuations of the light signal for the first, and second wavelengths;
   determining the blood oxygen saturation level within the subject's tissue using said ratio.

40. The method of claim 39, wherein the sensor is calibrated using the equation:

$$SmvO_2 = Kv*SvO_2 + Ka*SaO_2.$$

41. The method of claim 40, wherein the sensor is calibrated by using empirical data to determine a first calibration constant and a second calibration constant.

42. The method of claim 41, wherein the step of determining the ratio R of attenuations of the light signal for the first, and second wavelengths utilizes the equation:

$$R = \frac{A'_1 - E'_1}{A'_2 - E'_2}$$

where $E'_1$ represents the first calibration constant, $E'_2$ represents the second calibration constant, $A'_1$ represents the first attenuation of light signal of the first wavelength, and $A'_2$ represents the second attenuation of light signal of the second wavelength.

43. The method of claim 42, wherein the step of determining the first attenuation of the first wavelength utilizes the equation:

$$-\log (I_b/I_x)_1 = (\alpha_{r1}[Hb]_b + \alpha_{o1}[HbO_2]_b)L_b + (E-E_x)_1.$$

and the step of determining the second attenuation of the second wavelength utilizes the equation:

$$-\log (I_b/I_x)_2 = (\alpha_{r2}[Hb]_b + \alpha_{o2}[HbO_2]_b)L_b + (E-E_x)_2.$$

44. The method of claim 40, wherein the step of determining the blood oxygen saturation level within the subject's tissue utilizes the equation:

$$SnO_2\% = \frac{\alpha_{r1} - \alpha_{r2}R}{(\alpha_{r1} - \alpha_{o1}) + (\alpha_{o2} - \alpha_{r2})R} 100\%$$

where R represents the ratio of attenuations of the light signal for each of the first, and second wavelengths.

45. The method of claim 44, wherein the step of determining the ratio R of attenuations of the light signal for the first, and second wavelengths utilizes the equations:

$$R = \frac{A'_1 - E'_1}{A'_2 - E'_2}$$

where $E'_1$ represents the first calibration constant, $E'_2$ represents the second calibration constant, $A'_1$ represents the first attenuation of light signal of the first wavelength, and $A'_2$ represents the second attenuation of light signal of the second wavelength.

46. The method of claim 45, wherein the step of determining the first attenuation of the first wavelength utilizes the equation:

$$-\log (I_b/I_x)_1 = (\alpha_{r1}[Hb]_b + \alpha_{o1}[HbO_2]_b)L_b + (E-E_x)_1.$$

and the step of determining the second attenuation of the second wavelength utilizes the equation:

$$-\log (I_b/I_x)_2 = (\alpha_{r2}[Hb]_b + \alpha_{o2}[HbO_2]_b)L_b + (E-E_x)_2.$$

47. The method of claim 40, wherein the step of determining the blood oxygen saturation level within the subject's tissue comprising the steps of:
   determining the attenuation ratio R of the light signal for each of the first, and second wavelengths;
   determining the blood oxygen saturation level utilizing an empirical obtained calibration curve defining the relationship between the said attenuation ratio R with blood oxygen saturation.

48. The method of claim 47, wherein the step of determining the first attenuation of the first wavelength utilizes the equation:

$$A'_1 = -\log (I_b/I_x)_1 = (\alpha_{r1}[Hb]_b + \alpha_{o1}[HbO_2]_b)L_b + E'_1.$$

and the step of determining the second attenuation of the second wavelength utilizes the equation:

$$A'_2 = -\log (I_b/I_x)_2 = (\alpha_{r2}[Hb]_b + \alpha_{o2}[HbO_2]_b)L_b + E'_2.$$

49. The method of claim 48, wherein the concentration of oxyhemoglobin and the concentration of deoxyhemogiobin within the subject's tissue are determined using the equation:

$$\begin{bmatrix} A'_1 \\ A'_2 \end{bmatrix} \begin{bmatrix} \alpha_{r1} & \alpha_{o1} \\ \alpha_{r2} & \alpha_{o2} \end{bmatrix}^{-1} (L_b)^{-1} - \begin{bmatrix} E'_1 \\ E'_2 \end{bmatrix} \begin{bmatrix} \alpha_{r1} & \alpha_{o1} \\ \alpha_{r2} & \alpha_{o2} \end{bmatrix}^{-1} (L_b)^{-1} = \begin{bmatrix} [Hb]_b \\ [HbO_2]_b \end{bmatrix}$$

50. The method of claim 40, further comprising the steps of:

determining a photon pathlength $L_b$; and determining a concentration of oxyhemoglobin and a concentration of deoxyhemoglobin within the subject's tissue using the first and second calibration constants.

* * * * *

UNITED STATES PATENT AND TRADEMARK OFFICE
CERTIFICATE OF CORRECTION

| | | |
|---|---|---|
| PATENT NO. | : 7,072,701 B2 | Page 1 of 1 |
| APPLICATION NO. | : 10/628068 | |
| DATED | : July 4, 2006 | |
| INVENTOR(S) | : Chen et al. | |

It is certified that error appears in the above-identified patent and that said Letters Patent is hereby corrected as shown below:

Column 9, line 56, please delete "pathiength" and insert "pathlength".

Column 11, line 42, please delete "physioloqical" and insert "physiological."

Signed and Sealed this

Twenty-ninth Day of August, 2006

JON W. DUDAS
*Director of the United States Patent and Trademark Office*